(12) United States Patent  
Sonderegger et al.

(10) Patent No.: US 10,357,636 B2  
(45) Date of Patent: Jul. 23, 2019

(54) IV ACCESS DEVICE HAVING AN ANGLED PADDLE GRIP

(71) Applicant: Becton, Dickinson and Company, Franklin Lakes, NJ (US)

(72) Inventors: Ralph L. Sonderegger, Farmington, UT (US); Bart D. Peterson, Farmington, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 197 days.

(21) Appl. No.: 15/286,198

(22) Filed: Oct. 5, 2016

(65) Prior Publication Data

US 2017/0120012 A1 May 4, 2017

Related U.S. Application Data

(60) Provisional application No. 62/247,621, filed on Oct. 28, 2015, provisional application No. 62/247,596, (Continued)

(51) Int. Cl.
*A61M 25/00* (2006.01)
*A61M 25/06* (2006.01)

(52) U.S. Cl.
CPC .... *A61M 25/0606* (2013.01); *A61M 25/0637* (2013.01); *A61M 25/0693* (2013.01); *A61M 25/0097* (2013.01)

(58) Field of Classification Search
CPC .......... A61M 25/0606; A61M 25/0637; A61M 25/0693

(Continued)

(56) References Cited

U.S. PATENT DOCUMENTS 3,046,984 A 7/1962 Eby  
3,547,119 A 12/1970 Hall et al.  
(Continued)

FOREIGN PATENT DOCUMENTS

CA 2 133 053 A1 3/1995  
CN 101879341 A 11/2010  
(Continued)

OTHER PUBLICATIONS

Silva, Elson, Email Regarding "Respecting Hydrology Science and IP Rights—US Pat. Application 20110130728," pp. 1-6 (Jun. 2, 2011).

*Primary Examiner* — Phillip A Gray  
(74) *Attorney, Agent, or Firm* — Kirton & McConkie; Lloyd Metcalf; Kevin Stinger (57) ABSTRACT

An IV access device can include a needle hub having an angled paddle grip to facilitate insertion of the catheter at a low angle. The angled paddle grip can also minimize any interference that an extension tube or stabilization platform may cause during insertion. By employing an angled paddle grip, the catheter can be inserted while maintaining the stabilization platform in an orientation that is substantially parallel to the patient's skin. Also, in cases where the extension tube may run parallel with the stabilization platform, the angled paddle grip can prevent the extension tube from extending into the patient's skin during insertion. This will prevent the stabilization platform and/or the extension tube from catching on the patient's skin or otherwise inhibiting a smooth insertion of the catheter.

20 Claims, 8 Drawing Sheets

Related U.S. Application Data filed on Oct. 28, 2015, provisional application No. 62/296,383, filed on Feb. 17, 2016, provisional application No. 62/247,599, filed on Oct. 28, 2015, provisional application No. 62/247,617, filed on Oct. 28, 2015, provisional application No. 62/247,607, filed on Oct. 28, 2015, provisional application No. 62/247,624, filed on Oct. 28, 2015, provisional application No. 62/247,626, filed on Oct. 28, 2015, provisional application No. 62/296,385, filed on Feb. 17, 2016.

(58) Field of Classification Search
USPC .................................................. 604/164
See application file for complete search history.

(56) References Cited

U.S. PATENT DOCUMENTS

| | | |
|---|---|---|
| 3,589,361 A | 6/1971 | Loper et al. |
| 3,827,434 A | 8/1974 | Thompson et al. |
| 3,853,127 A | 12/1974 | Spademan |
| 3,859,998 A | 1/1975 | Thomas et al. |
| 4,003,403 A | 1/1977 | Nehring |
| 4,043,346 A | 8/1977 | Mobley et al. |
| 4,099,528 A | 7/1978 | Sorenson et al. |
| 4,149,539 A | 4/1979 | Cianci |
| 4,172,448 A | 10/1979 | Brush |
| 4,177,809 A | 12/1979 | Moorehead |
| 4,193,399 A | 3/1980 | Robinson |
| 4,200,096 A | 4/1980 | Charvin |
| 4,269,186 A | 5/1981 | Loveless et al. |
| 4,311,137 A | 1/1982 | Gerard |
| 4,317,445 A | 3/1982 | Robinson |
| 4,326,519 A | 4/1982 | D'Alo et al. |
| 4,353,369 A | 10/1982 | Muetterties et al. |
| 4,362,156 A | 12/1982 | Feller, Jr. et al. |
| 4,365,630 A | 12/1982 | McFarlane |
| 4,387,879 A | 6/1983 | Tauschinski |
| 4,419,094 A | 12/1983 | Patel |
| 4,449,693 A | 5/1984 | Gereg |
| 4,496,348 A | 1/1985 | Genese et al. |
| 4,525,157 A | 6/1985 | Vaillancourt |
| 4,531,935 A | 7/1985 | Berryessa |
| 4,682,980 A | 7/1987 | Suzuki |
| 4,701,162 A | 10/1987 | Rosenberg |
| 4,703,761 A | 11/1987 | Rathbone et al. |
| 4,758,225 A | 7/1988 | Cox et al. |
| 4,765,588 A | 8/1988 | Atkinson |
| 4,772,264 A | 9/1988 | Cragg |
| 4,813,939 A | 3/1989 | Marcus |
| 4,834,708 A * | 5/1989 | Pillari ............... A61M 25/0637 |
| | | 604/165.04 |
| 4,842,591 A | 6/1989 | Luther |
| 4,874,377 A | 10/1989 | Newgard et al. |
| 4,894,052 A | 1/1990 | Crawford |
| 4,917,668 A | 4/1990 | Haindl |
| 4,917,671 A | 4/1990 | Chang |
| 4,925,444 A | 5/1990 | Orkin et al. |
| 4,935,010 A | 6/1990 | Cox et al. |
| 4,950,257 A | 8/1990 | Hibbs et al. |
| 4,966,586 A | 10/1990 | Vaillancourt |
| D315,822 S | 3/1991 | Ryan |
| 5,032,116 A | 7/1991 | Peterson et al. |
| 5,041,097 A | 8/1991 | Johnson |
| 5,053,014 A | 10/1991 | Van Heugten |
| 5,057,087 A | 10/1991 | Harmon |
| 5,059,186 A | 10/1991 | Yamamoto et al. |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,108,374 A | 4/1992 | Lemieux |
| 5,127,905 A | 7/1992 | Lemieux |
| 5,135,504 A | 8/1992 | McLees |
| 5,154,703 A | 10/1992 | Bonaldo |
| 5,156,596 A | 10/1992 | Balbierz et al. |
| 5,176,653 A | 1/1993 | Metais |
| 5,176,662 A | 1/1993 | Bartholomew et al. |
| 5,201,717 A | 4/1993 | Wyatt et al. |
| 5,211,634 A | 5/1993 | Vaillancourt |
| 5,215,525 A | 6/1993 | Sturman |
| 5,215,528 A | 6/1993 | Purdy et al. |
| 5,215,529 A | 6/1993 | Fields et al. |
| 5,226,883 A | 7/1993 | Katsaros et al. |
| 5,234,410 A | 8/1993 | Graham et al. |
| 5,242,411 A | 9/1993 | Yamamoto et al. |
| 5,254,097 A | 10/1993 | Schock et al. |
| 5,267,971 A | 12/1993 | Brimhall |
| 5,269,764 A | 12/1993 | Vetter et al. |
| 5,273,546 A | 12/1993 | McLaughlin et al. |
| 5,290,222 A | 3/1994 | Feng et al. |
| 5,290,246 A | 3/1994 | Yamamoto et al. |
| 5,295,969 A | 3/1994 | Fischell et al. |
| 5,306,243 A | 4/1994 | Bonaldo |
| 5,312,359 A | 5/1994 | Wallace |
| 5,328,482 A | 7/1994 | Sircom et al. |
| 5,330,435 A | 7/1994 | Vaillancourt |
| 5,342,315 A | 8/1994 | Rowe et al. |
| 5,350,363 A | 9/1994 | Goode et al. |
| 5,352,205 A | 10/1994 | Dales et al. |
| 5,356,381 A | 10/1994 | Ensminger et al. |
| 5,368,029 A | 11/1994 | Holcombe et al. |
| 5,405,323 A | 4/1995 | Rogers et al. |
| 5,447,501 A | 9/1995 | Karlsson et al. |
| 5,456,675 A | 10/1995 | Wolbring et al. |
| 5,458,658 A | 10/1995 | Sircom |
| 5,487,728 A | 1/1996 | Vaillancourt |
| 5,509,912 A | 4/1996 | Vaillancourt et al. |
| 5,520,666 A | 5/1996 | Choudhury et al. |
| 5,542,932 A | 8/1996 | Daugherty |
| 5,549,566 A | 8/1996 | Elias et al. |
| 5,549,576 A | 8/1996 | Patterson et al. |
| 5,549,577 A | 8/1996 | Siegel et al. |
| 5,562,631 A | 10/1996 | Bogert |
| 5,562,633 A | 10/1996 | Wozencroft |
| 5,573,510 A | 11/1996 | Isaacson |
| 5,575,769 A | 11/1996 | Vaillancourt |
| 5,575,777 A | 11/1996 | Cover et al. |
| 5,584,809 A | 12/1996 | Gaba |
| 5,599,310 A | 2/1997 | Bogert |
| 5,601,536 A | 2/1997 | Crawford et al. |
| 5,613,663 A | 3/1997 | Schmidt et al. |
| 5,651,772 A | 7/1997 | Arnett |
| 5,657,963 A | 8/1997 | Hinchliffe et al. |
| 5,676,656 A | 10/1997 | Brimhall |
| 5,690,612 A | 11/1997 | Lopez et al. |
| 5,690,619 A | 11/1997 | Erskine |
| 5,697,907 A | 12/1997 | Gaba |
| 5,697,914 A | 12/1997 | Brimhall |
| 5,697,915 A | 12/1997 | Lynn |
| 5,699,821 A | 12/1997 | Paradis |
| 5,700,244 A | 12/1997 | Kriesel |
| 5,700,250 A | 12/1997 | Erskine |
| 5,704,919 A | 1/1998 | Kraus et al. |
| 5,718,688 A | 2/1998 | Wozencroft |
| 5,730,123 A | 3/1998 | Lorenzen et al. |
| 5,738,144 A | 4/1998 | Rogers |
| 5,749,856 A | 5/1998 | Zadini et al. |
| 5,749,861 A | 5/1998 | Guala et al. |
| 5,772,636 A | 6/1998 | Brimhall et al. |
| 5,800,399 A | 9/1998 | Bogert et al. |
| 5,806,831 A | 9/1998 | Paradis |
| 5,810,780 A | 9/1998 | Brimhall et al. |
| 5,817,069 A | 10/1998 | Arnett |
| 5,843,046 A | 12/1998 | Motisi et al. |
| 5,853,393 A | 12/1998 | Bogert |
| 5,882,345 A | 3/1999 | Yoon |
| 5,911,710 A | 6/1999 | Barry et al. |
| 5,935,109 A | 8/1999 | Donnan |
| 5,935,110 A | 8/1999 | Brimhall |
| 5,947,932 A | 9/1999 | Desecki et al. |
| 5,954,698 A | 9/1999 | Pike |
| 5,961,497 A | 10/1999 | Larkin |

(56) References Cited

U.S. PATENT DOCUMENTS

| | | |
|---|---|---|
| 5,967,490 A | 10/1999 | Pike |
| 6,039,302 A | 3/2000 | Cote, Sr. et al. |
| 6,056,726 A | 5/2000 | Isaacson |
| 6,077,244 A | 6/2000 | Botich et al. |
| 6,117,108 A | 9/2000 | Woehr et al. |
| 6,142,981 A | 11/2000 | Heck et al. |
| 6,171,287 B1 | 1/2001 | Lynn et al. |
| 6,206,851 B1 | 3/2001 | Prosl |
| 6,221,047 B1 | 4/2001 | Greene et al. |
| 6,224,569 B1 | 5/2001 | Brimhall |
| 6,273,869 B1 | 8/2001 | Vaillancourt |
| 6,287,278 B1 | 9/2001 | Woehr et al. |
| D451,600 S | 12/2001 | Crawford et al. |
| 6,379,332 B1 | 4/2002 | Van Landuyt |
| D458,678 S | 6/2002 | Cindrich |
| D458,994 S | 6/2002 | Cindrich |
| 6,461,362 B1 | 10/2002 | Halseth et al. |
| 6,485,473 B1 | 11/2002 | Lynn |
| 6,497,994 B1 | 12/2002 | Kafrawy |
| 6,506,181 B2 | 1/2003 | Meng et al. |
| D469,870 S | 2/2003 | Niermann et al. |
| 6,565,542 B2 | 5/2003 | Kumar et al. |
| 6,575,960 B2 | 6/2003 | Becker et al. |
| 6,595,954 B1 | 7/2003 | Luther et al. |
| 6,595,981 B2 | 7/2003 | Huet |
| 6,616,630 B1 | 9/2003 | Woehr et al. |
| 6,652,486 B2 | 11/2003 | Bialecki et al. |
| 6,663,592 B2 | 12/2003 | Rhad et al. |
| 6,689,102 B2 | 2/2004 | Greene |
| 6,695,814 B2 | 2/2004 | Greene et al. |
| 6,699,221 B2 | 3/2004 | Vaillancourt |
| 6,709,419 B2 | 3/2004 | Woehr |
| 6,719,726 B2 | 4/2004 | Meng et al. |
| 6,740,063 B2 | 5/2004 | Lynn |
| D491,266 S | 6/2004 | Cindrich et al. |
| D492,031 S | 6/2004 | Cindrich et al. |
| 6,749,588 B1 | 6/2004 | Howell et al. |
| D492,774 S | 7/2004 | Cindrich et al. |
| 6,837,884 B2 | 1/2005 | Woloszko |
| 6,883,778 B1 | 4/2005 | Newton et al. |
| 7,008,404 B2 | 3/2006 | Nakajima |
| 7,347,839 B2 | 3/2008 | Hiejima |
| 7,396,346 B2 | 7/2008 | Nakajima |
| 7,470,254 B2 | 12/2008 | Basta et al. |
| D592,302 S | 5/2009 | Stokes et al. |
| 7,670,317 B2 | 3/2010 | Cindrich et al. |
| 7,694,403 B2 | 4/2010 | Moulton |
| 7,736,339 B2 | 6/2010 | Woehr et al. |
| 7,905,856 B2 | 3/2011 | McGuckin, Jr. et al. |
| 7,914,494 B2 | 3/2011 | Hiejima |
| 8,066,670 B2 | 11/2011 | Cluff et al. |
| 8,066,675 B2 | 11/2011 | Cindrich et al. |
| 8,070,725 B2 | 12/2011 | Christensen |
| 8,357,119 B2 | 1/2013 | Stout et al. |
| 8,361,020 B2 | 1/2013 | Stout et al. |
| 8,388,583 B2 | 3/2013 | Stout et al. |
| 8,574,203 B2 | 11/2013 | Stout et al. |
| 8,597,252 B2 | 12/2013 | Burkholz et al. |
| 8,641,675 B2 | 2/2014 | Stout et al. |
| 8,679,063 B2 | 3/2014 | Stout et al. |
| D713,522 S | 9/2014 | Woehr et al. |
| 2001/0053895 A1 | 12/2001 | Vaillancourt |
| 2002/0072712 A1 | 6/2002 | Nool et al. |
| 2002/0082546 A1 | 6/2002 | Crank et al. |
| 2002/0177814 A1 | 11/2002 | Meng et al. |
| 2003/0083620 A1 | 5/2003 | Luther et al. |
| 2004/0078003 A1 | 4/2004 | Smith et al. |
| 2004/0092889 A1 | 5/2004 | Ferguson et al. |
| 2004/0102735 A1 | 5/2004 | Moulton et al. |
| 2004/0181192 A1 | 9/2004 | Cuppy |
| 2004/0193112 A1 | 9/2004 | Glazier et al. |
| 2004/0204681 A1 | 10/2004 | Thoresen et al. |
| 2004/0225260 A1 | 11/2004 | Villa et al. |
| 2004/0243060 A1 | 12/2004 | Rossi et al. |
| 2004/0243061 A1 | 12/2004 | McGurk |
| 2005/0273019 A1 | 12/2005 | Conway et al. |
| 2005/0277879 A1 | 12/2005 | Daga |
| 2006/0163515 A1 | 7/2006 | Ruschke |
| 2007/0043334 A1 | 2/2007 | Guala |
| 2007/0083157 A1 | 4/2007 | Belley et al. |
| 2007/0083162 A1 | 4/2007 | O'Reagan et al. |
| 2007/0093778 A1 | 4/2007 | Cindrich et al. |
| 2007/0191777 A1 | 8/2007 | King |
| 2007/0225648 A1 | 9/2007 | Winsor et al. |
| 2007/0233007 A1 | 10/2007 | Adams |
| 2008/0039796 A1 | 2/2008 | Nakajima |
| 2008/0108944 A1 | 5/2008 | Woehr et al. |
| 2008/0132832 A1 | 6/2008 | McKinnon et al. |
| 2008/0255473 A1 | 10/2008 | Dalebout et al. |
| 2008/0287906 A1 | 11/2008 | Burkholz et al. |
| 2009/0054845 A1 | 2/2009 | Puhasmagi et al. |
| 2009/0099431 A1 | 4/2009 | Dalebout et al. |
| 2009/0287189 A1 | 11/2009 | Suwito |
| 2010/0204648 A1 | 8/2010 | Stout et al. |
| 2010/0204675 A1 | 8/2010 | Woehr et al. |
| 2010/0222746 A1 | 9/2010 | Burkholz |
| 2010/0280455 A1 | 11/2010 | Ogawa et al. |
| 2011/0046570 A1 | 2/2011 | Stout et al. |
| 2011/0054403 A1 | 3/2011 | Tanabe et al. |
| 2011/0130728 A1 | 6/2011 | McKinnon |
| 2012/0016265 A1 | 1/2012 | Peterson et al. |
| 2012/0016307 A1 | 1/2012 | Burkholz et al. |
| 2012/0053523 A1 | 3/2012 | Harding |
| 2013/0090608 A1 | 4/2013 | Stout et al. |
| 2013/0218082 A1 | 8/2013 | Hyer et al. |
| 2013/0237925 A1 | 9/2013 | Trainer et al. |
| 2014/0046258 A1 | 2/2014 | Stout et al. |
| 2014/0107584 A1 | 4/2014 | Rosenberg et al. |
| 2014/0364809 A1 | 12/2014 | Isaacson et al. |
| 2015/0224296 A1 | 8/2015 | Winsor |
| 2017/0120008 A1 | 5/2017 | Burkholz et al. |
| 2017/0120014 A1 | 5/2017 | Harding et al. |
| 2017/0216535 A1 | 8/2017 | Mao |

FOREIGN PATENT DOCUMENTS

| | | |
|---|---|---|
| CN | 102440822 A | 5/2012 |
| CN | 102716541 A | 10/2012 |
| CN | 203852671 | 10/2014 |
| DE | 20 2009 009 602 U1 | 12/2009 |
| EP | 0 268 480 A1 | 5/1988 |
| EP | 0 732 120 A1 | 9/1996 |
| EP | 0 812 601 A2 | 12/1997 |
| EP | 0 993 839 A1 | 4/2000 |
| EP | 1 306 097 | 5/2003 |
| EP | 1 679 043 A1 | 7/2006 |
| EP | 1 884 257 A1 | 2/2008 |
| EP | 1 944 049 A1 | 7/2008 |
| EP | 2022421 | 2/2009 |
| EP | 2 044 970 A1 | 4/2009 |
| EP | 2 327 434 A1 | 6/2011 |
| GB | 2508466 A | 6/2014 |
| JP | 2011045544 | 3/2011 |
| JP | 2014108112 | 6/2014 |
| WO | 88/07388 A1 | 10/1988 |
| WO | 97/45151 | 12/1997 |
| WO | 98/42393 A1 | 10/1998 |
| WO | 99/34849 A1 | 7/1999 |
| WO | 01/12254 A1 | 2/2001 |
| WO | 02/096495 | 12/2002 |
| WO | 2004/032995 A2 | 4/2004 |
| WO | 2004/082727 | 9/2004 |
| WO | 2004/087247 | 10/2004 |
| WO | 2004/098685 A1 | 11/2004 |
| WO | 2006/037638 A1 | 4/2006 |
| WO | 2008/022258 A2 | 2/2008 |
| WO | 2008/045761 A2 | 4/2008 |
| WO | 2008/052790 A2 | 5/2008 |
| WO | 2008/058132 A2 | 5/2008 |
| WO | 2008/058133 A2 | 5/2008 |
| WO | 2009/114833 A1 | 9/2009 |
| WO | 2010/093791 A1 | 8/2010 |
| WO | 2010/111283 | 9/2010 |
| WO | 2010/111285 A1 | 9/2010 |

(56) References Cited

FOREIGN PATENT DOCUMENTS

| WO | 2011/055287 | 5/2011 |
| WO | 2011/109542 A1 | 9/2011 |
| WO | 2016/007442 | 1/2016 |
| WO | 2017/062579 | 4/2017 |

\* cited by examiner

IV ACCESS DEVICE HAVING AN ANGLED PADDLE GRIP

RELATED APPLICATIONS

This application claims the benefit of U.S. Provisional Patent Application Ser. No. 62/247,621, which was filed Oct. 28, 2015, U.S. Provisional Patent Application No. 62/247,596, which was filed on Oct. 28, 2015, U.S. Provisional Patent Application No. 62/296,383, which was filed on Feb. 17, 2016, U.S. Provisional Patent Application No. 62/247,599, which was filed Oct. 28, 2015, U.S. Provisional Patent Application No. 62/247,617, which was filed on Oct. 28, 2015, U.S. Provisional Patent Application Ser. No. 62/247,607, which was filed Oct. 28, 2015, U.S. Provisional Patent Application Ser. No. 62/247,624, which was filed Oct. 28, 2015, U.S. Provisional Application No. 62/247,626, which was filed on Oct. 28, 2015, and U.S. Provisional Application No. 62/296,385, which was filed on Feb. 17, 2016, each of which is incorporated herein by reference in their entirety.

BACKGROUND

When an IV access device is identified as being "closed" or "integrated," it generally refers to the fact that the device is configured to prevent blood from escaping the device during insertion of the catheter. Typically, such IV access devices accomplish this by integrating an extension set with the catheter adapter.

Figure 1:
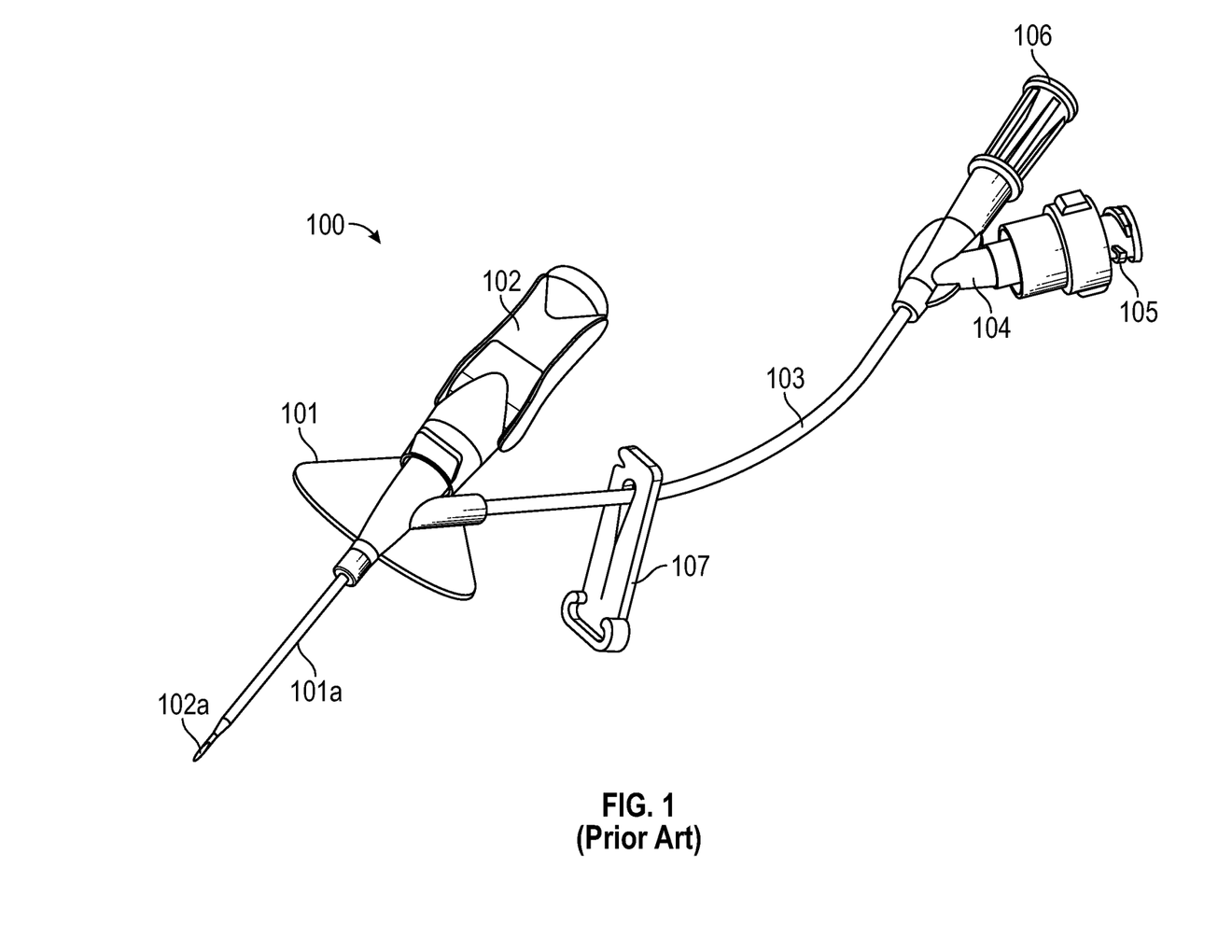
FIG. 1 illustrates a PRIOR ART IV access device.

FIG. 1 illustrates an example of a PRIOR ART closed IV access device 100. Device 100 includes a catheter adapter 101 from which a catheter 101a extends, a needle hub 102 from which a needle 102a extends, an extension tube 103 that is coupled to catheter adapter 101 at one end and includes a Y-adapter 104 coupled to the other end, and a clamp 107 for blocking or limiting fluid flow through extension tube 103. Y-adapter 104 includes a port 105 and a vent plug 106. Device 100 can be a closed system by incorporating fluid flow blocking components (e.g., a septum or vent) into each external opening of the device such as into a proximal end of catheter adapter 101 and into any ports in adapter 104.

Oftentimes, when using an IV access device such as access device 100, the clinician will grip catheter adapter 101 and/or needle hub 102 with the thumb on top and one or more fingers underneath. Also, if catheter adapter 101 includes a stabilization platform, such as is shown in FIG. 1, the clinician may grip a portion of the stabilization platform opposite extension tube 103. When this type of insertion technique is employed, it is difficult to position catheter adapter 101 at a low angle with respect to the patient's skin—something that is desirable to do to obtain proper placement of catheter 101a—since the clinician's fingers prevent catheter adapter 101 from being positioned close to the patient's skin.

To minimize the angle of insertion while gripping the stabilization platform of catheter adapter 101, a clinician may rotate catheter adapter 101 in a counter-clockwise direction (from the perspective of the clinician) thereby creating a space between the stabilization platform and the patient's skin within which the clinician's fingers may be positioned during insertion. However, rotating catheter adapter 101 in this manner will cause the other side of the stabilization platform, including extension tube 103, to be angled into the patient's skin. In such cases, the stabilization platform and extension tube may drag against or catch on the patient's skin thereby making a smooth insertion difficult.

BRIEF SUMMARY OF THE INVENTION

The present invention is generally directed to an IV access device that includes a needle hub having an angled paddle grip to facilitate insertion of the catheter at a low angle. The angled paddle grip can also minimize any interference that the extension tube or stabilization platform may cause during insertion. By employing an angled paddle grip, the catheter can be inserted while maintaining the stabilization platform in an orientation that is substantially parallel to the patient's skin. Also, because the extension tube runs parallel with the stabilization platform, the extension tube will not be extending into the patient's skin during insertion. This will prevent the extension tube from catching on the patient's skin or otherwise inhibiting a smooth insertion of the catheter.

A catheter adapter in accordance with the present invention can include a stabilization platform (e.g., wings) that may form a surface that can lay flat on the patient's skin. This stabilization platform can be flexible or otherwise repositionable to allow at least one side of the stabilization platform to be oriented at an angle during insertion of the catheter. To orient the stabilization platform at an angle, the needle hub can include an angled paddle grip that is designed to be positioned below the stabilization platform when the needle hub is coupled to the catheter adapter. Due to the flexibility or repositionability of the stabilization platform, the angled paddle grip will lift the stabilization platform to position it at a corresponding angle. The clinician may then grip the angled paddle grip and the angled stabilization platform when inserting the catheter. Due to the angling of these components, the catheter adapter can be maintained in a generally flat orientation during insertion. More particularly, the stabilization platform opposite the angled paddle grip as well as the extension tube will be maintained in a generally flat orientation during insertion thereby minimizing any likelihood that these components will drag against or snag on the patient's skin.

In one embodiment, the present invention is implemented as an IV access device that includes a catheter adapter from which a catheter extends distally, the catheter adapter including a wing; and a needle hub from which a needle extends distally, the needle hub being configured to be coupled to the catheter adapter such that the needle extends through the catheter. The needle hub further includes a paddle grip that is configured to be positioned adjacent the wing when the needle hub is coupled to the catheter adapter, the paddle grip being oriented at an angle.

In another embodiment, the present invention is implemented as an IV access device that includes a catheter adapter from which a catheter extends distally, the catheter adapter including a wing; and a needle hub from which a needle extends distally, the needle hub being configured to be coupled to the catheter adapter such that the needle extends through the catheter. The needle hub further includes a paddle grip that is configured to be positioned adjacent the wing when the needle hub is coupled to the catheter adapter. When the paddle grip is forced into contact with the wing, the paddle grip causes the wing to be elevated into an angled orientation.

In another embodiment, the present invention is implemented as an IV access device comprising a catheter adapter from which a catheter extends distally, the catheter adapter including a first wing that extends from a first side of the catheter adapter and a second wing that extends from a second side of the catheter adapter opposite the first side; an extension tube that couples to the catheter adapter on the second side; and a needle hub from which a needle extends distally. The needle hub is configured to be coupled to the catheter adapter such that the needle extends through the catheter. The needle hub includes a paddle grip that is configured to be positioned adjacent the first wing when the needle hub is coupled to the catheter adapter. The paddle grip causing the first wing to be positioned in an angled orientation.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

Figure 2:
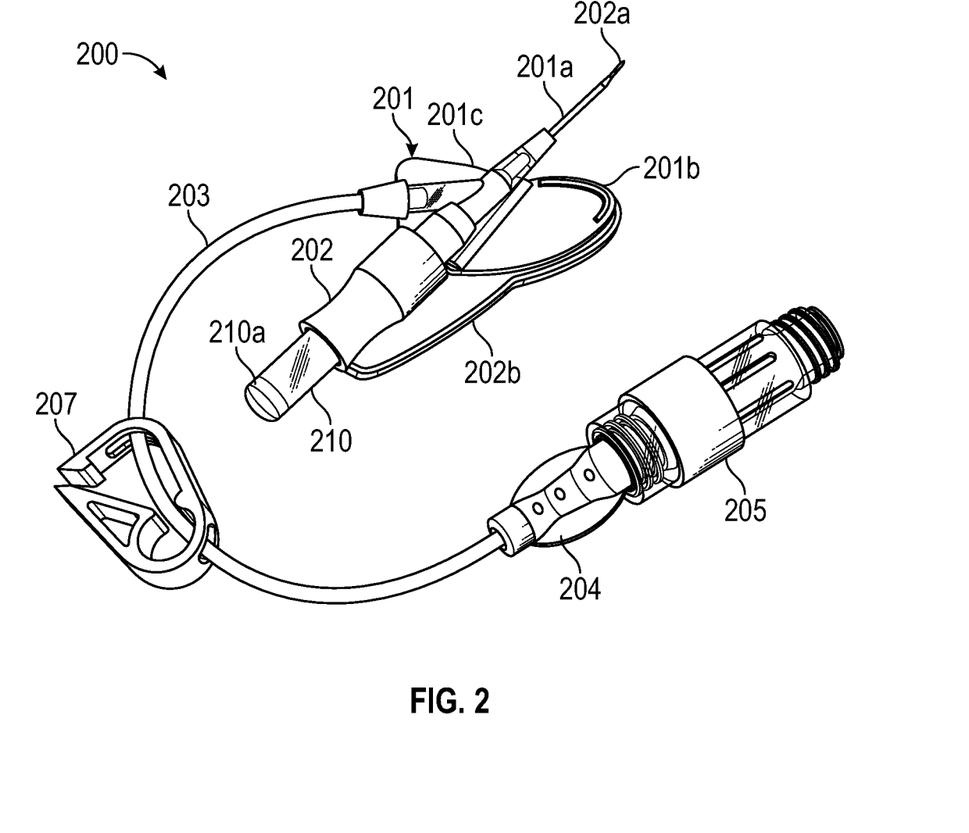
FIG. 2 illustrates an IV access device in accordance with one or more embodiments of the present invention.

FIG. 2 illustrates an example of a closed IV access device 200 that is configured in accordance with one or more embodiments of the present invention. Access device 200 includes a catheter adapter 201 from which a catheter 201a extends distally, a needle hub 202 from which a needle 202a extends distally, an extension tube 203 that is fluidly coupled to a lumen of catheter adapter 201, and a clamp 207 for restricting the flow of fluid through extension tube 203. A luer adapter 204 or other type of adapter can be coupled to the end of extension tube 203. Also, a luer access device 205, such as one that includes a septum, may be coupled to luer adapter 204.

Catheter adapter 201 can include a stabilization platform formed by wings 201b and 201c which extend outwardly from opposite sides of catheter adapter 201. As shown in FIG. 2, access device 200 is configured for right-hand use in that extension tube 203 couples to the left side of catheter adapter 201 such that wing 201b is fully exposed. This can facilitate gripping wing 201b with the thumb of the right hand. As shown, extension tube 203 can run substantially parallel with wing 201c.

Needle hub 202 includes a paddle grip 202b that extends outwardly from the right side of needle hub 202 and has a shape that generally corresponds to the shape of wing 201b. Accordingly, paddle grip 202b can be positioned directly beneath wing 201b so that wing 201b and paddle grip 202b can be sandwiched between the clinician's thumb and index finger during insertion of catheter 201a. Alternatively, paddle grip 202b could be configured to be positioned above or otherwise adjacent to wing 201b. By configuring paddle grip 202b in this manner, the clinician can easily withdraw needle hub 202 from catheter adapter 201 by simply sliding the index finger backwards with respect to the thumb thereby causing the paddle grip 202b to slide backward away from wing 201b.

In some embodiments, needle hub 202 may also include a flash chamber 210 that is coupled to the proximal end of needle hub 202. Flash chamber 210 can include a plug 210a that allows air to escape through a proximal opening in needle hub 202 while preventing blood from escaping. Also, a proximal end of needle 202a can extend into flash chamber 210 and can include an opening to allow blood to flow out of needle 202a and into flash chamber 210.

Figure 3A:
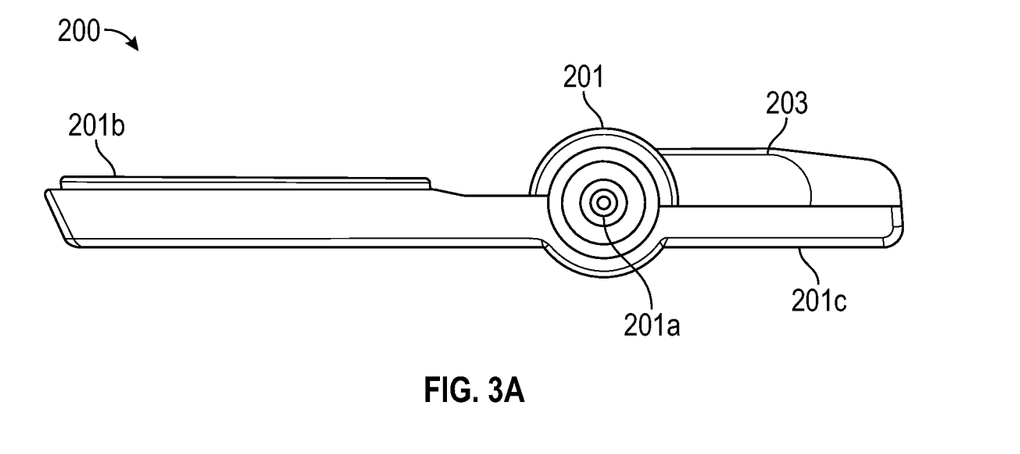
FIG. 3A illustrates a view of the catheter adapter of FIG. 2 separated from the needle hub.
Figure 3B:
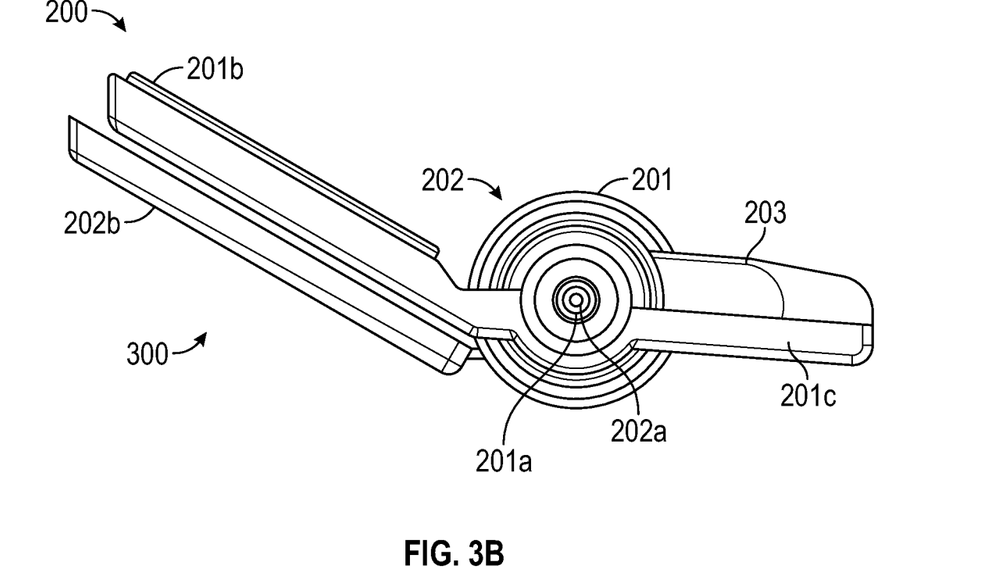
FIG. 3B illustrates a view of the catheter adapter of FIG. 2 when the needle hub is coupled to the catheter adapter.

In accordance with embodiments of the present invention, and as shown in FIGS. 3A and 3B, paddle grip 202b can be angled with respect to a flat orientation of catheter adapter 201. FIG. 3A illustrates catheter adapter 201 when needle hub 202 is not coupled thereto. As shown, wings 201b and 201c are configured to lay flat (e.g., within the same plane) to form a stabilization platform on the patient's skin. Extension tube 203 is also shown as extending substantially in parallel with wing 201c. In fact, in access device 200, the interface between extension tube 203 and catheter adapter 201 is formed into wing 201c.

In contrast, FIG. 3B illustrates the orientation of wing 201b when needle hub 202 is coupled to catheter adapter 201. Paddle grip 202b can be oriented at an angle to the flat orientation of wing 201b so that, when paddle grip 202b is positioned underneath and in contact with wing 201b, paddle grip 202b lifts wing 201b into the angled orientation depicted in FIG. 3B. Importantly, with wing 201b in this angled orientation, wing 201c remains in its flat orientation. The space 300 that is created underneath wing 201b and paddle grip 202b allows the clinician to position his or her fingers underneath paddle grip 202b while still maintaining catheter adapter 201 in its flat orientation.

More particularly, the clinician may place his or her thumb on top of wing 201b and one or more of his or her fingers under paddle grip 202b during insertion of catheter 201a while still maintaining catheter adapter 201 at a low angle with respect to the patient's skin and without having to rotate catheter adapter to cause wing 201c and extension tube 203 to extend towards the patient's skin. In this way, the angled paddle grip 202b can facilitate a smooth insertion of catheter 201a at a low angle.

After the catheter has been properly placed in a patient's vein, needle hub 202 can be withdrawn from catheter adapter 201. Withdrawing needle hub 202 will likewise cause paddle grip 202b to be withdrawn such that it no longer supports wing 201b in the angled orientation. As a result, wing 201b can return to its flat orientation to facilitate securing catheter adapter 201 against the patient's skin. Accordingly, the design of access device 200 facilitates inserting catheter 201a at a low angle while still allowing catheter adapter 201 to be secured comfortably to the patient's skin.

FIGS. 3A and 3B depict an embodiment where wing 201b is formed of a flexible material that allows it to be positioned in the angled orientation. In some embodiments, a flexible material of the present invention comprises a hardness of from approximately 30 Shore A to approximately 90 Shore D. In some embodiments, a flexible material comprises a durometer hardness of from approximately 50 Shore A to approximately 90 Shore D. In some embodiments, wing 201c may be formed of the same or similar flexible material as wing 201b. In other embodiments, wing 201b (and possibly wing 201c) may be coupled to catheter adapter 201 via a hinged connection that allows the wing to pivot between the flat orientation and the angled orientation. A hinged connection may be preferred when wing 201b and/or wing 201c is formed of a rigid or semi-rigid material. In some cases, the flexibility of a wing may be created by forming a thin section within the wing. For example, a portion of the wing that extends along the length of the catheter adapter may be thinner than other portions of the wing so that the wing is allowed to bend along the thinner portion.

As indicated above, FIGS. 2, 3A, and 3B depict an access device that is designed for right-handed insertion. By inverting the depicted design, an access device configured for left-handed insertion would be formed. Also, even though the invention has primarily been described with reference to an access device that includes an extension tube (e.g., a closed or integrated device), an angled paddle grip could be employed with any type of catheter adapter having a stabilization platform consisting of at least one wing including those that do not include an extension tube.

In some embodiments, a needle hub may be configured to include two paddle grips for positioning both wings at an angled orientation. FIGS. 4A-4E and 5A-5B illustrate examples of such a two paddle grip configuration.

Figure 4A:
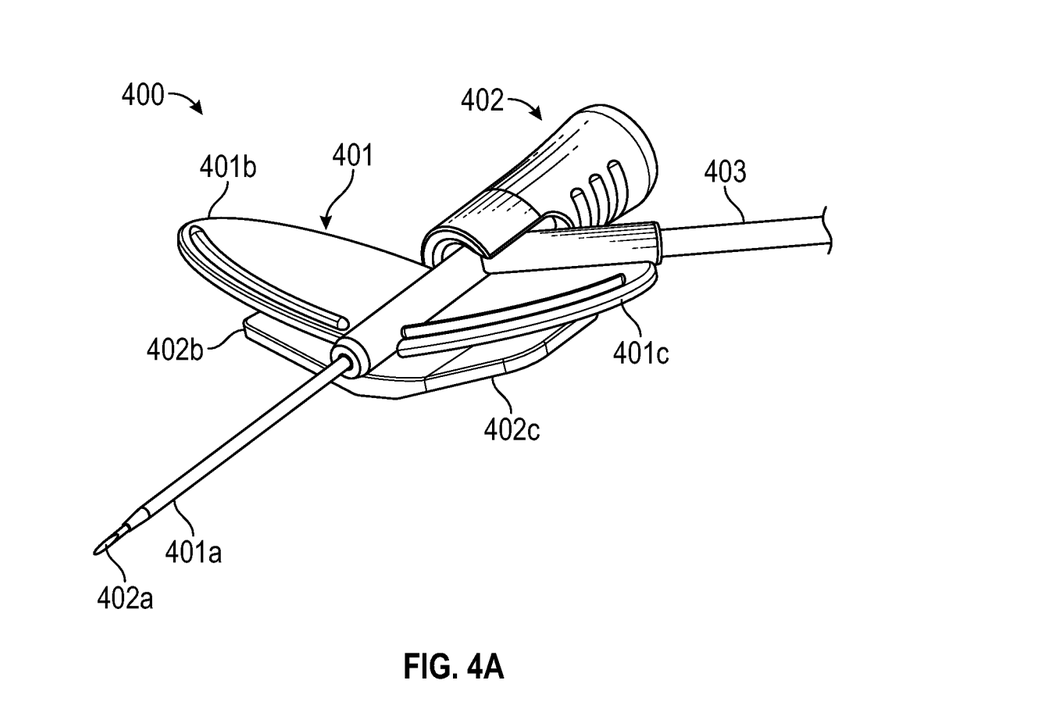
FIGS. 4A-4E illustrate various views of another access device configured in accordance with one or more embodiments of the present invention.

In FIG. 4A, an access device 400 similar to access device 200 is depicted. Access device 400 includes a catheter adapter 401 having a catheter 401a, a needle hub 402 that secures a needle 402a, and an extension tube 403 that extends from catheter adapter 401. Catheter adapter 401 includes two wings 401b and 401c that extend from opposite sides of catheter adapter 401. Both wings 401b and 401c are flexible to allow them to be positioned in an angled orientation. Needle hub 402 includes two paddle grips 402b and 402c that are configured to be positioned underneath wings 401b and 401c respectively when needle hub 402 is coupled to catheter adapter 401.

Figure 4B:
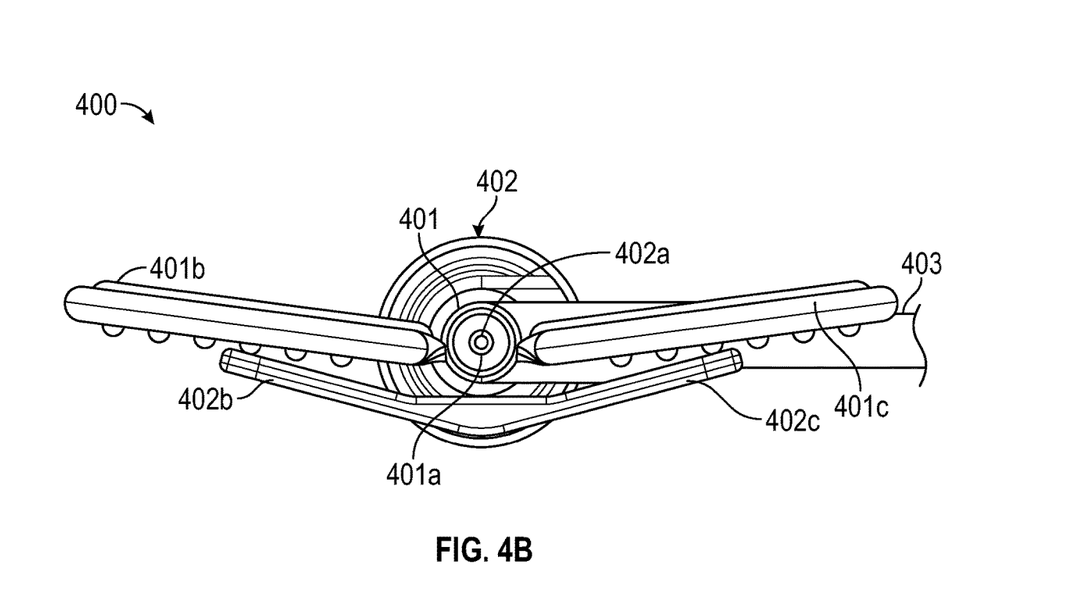
Figure 4C:
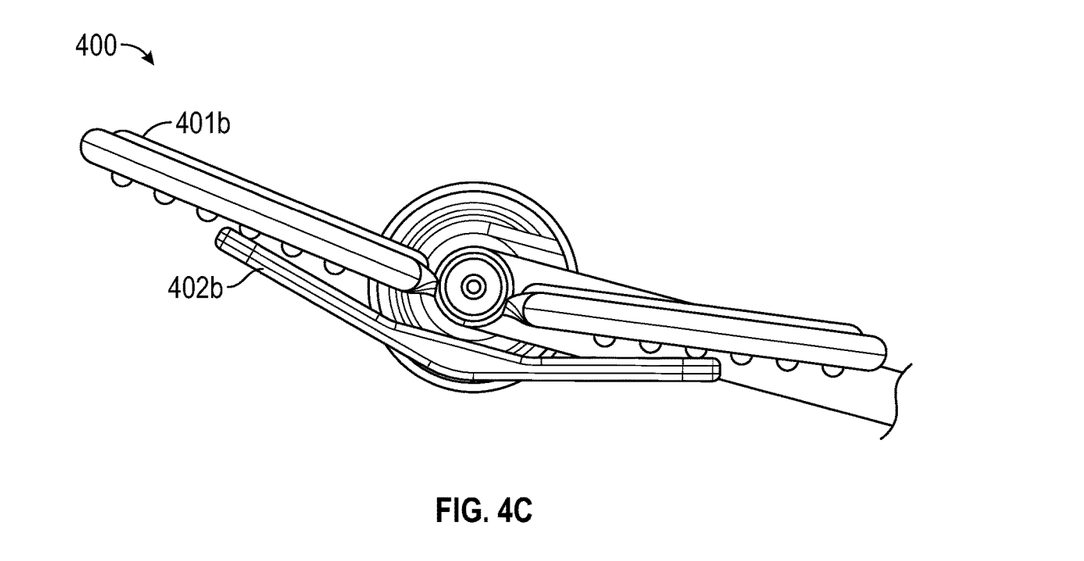
Figure 4D:
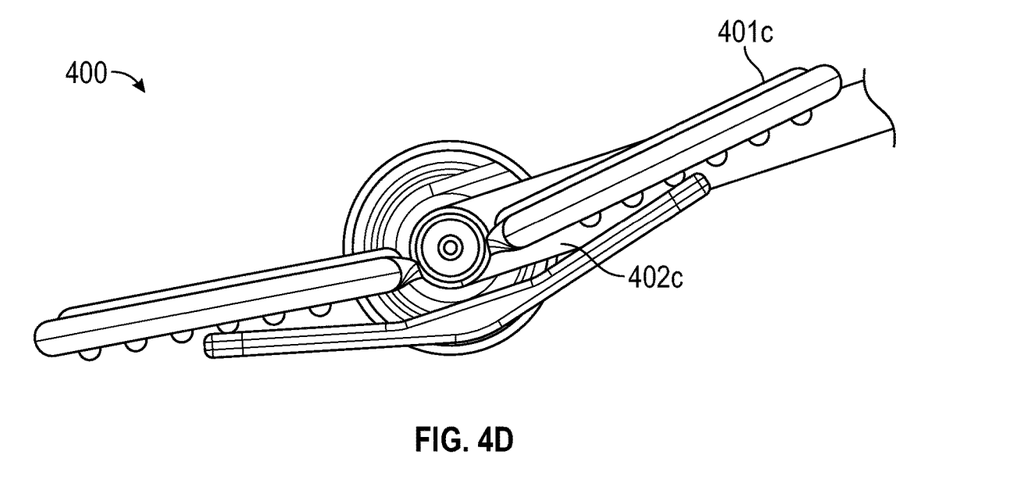

As best shown in FIG. 4B, paddle grips 402b and 402c are oriented at an angle so that wings 401b and 401c are lifted into a corresponding angled orientation. By orienting both wings 401b and 401c at an angle, catheter 401a can more easily be inserted at a low angle. For example, as represented in FIG. 4C, if a right-handed user were to grip paddle grip 402b and wing 401b, the user could rotate catheter adapter 401 slightly in a counterclockwise direction without causing wing 401c to be extended towards the patient's skin. In other words, by angling wing 401c in addition to wing 401b, more space can be created underneath wing 401b and paddle grip 402b to accommodate the user's fingers without having to increase the angle of insertion and while still maintaining wing 401c in a generally parallel orientation with respect to the patient's skin. Similarly, as represented in FIG. 4D, a left-handed user could grip wing 401c and paddle grip 402c during insertion and rotate catheter adapter 401 in a clockwise direction without causing wing 401b to be extended into the patient's skin.

Figure 4E:
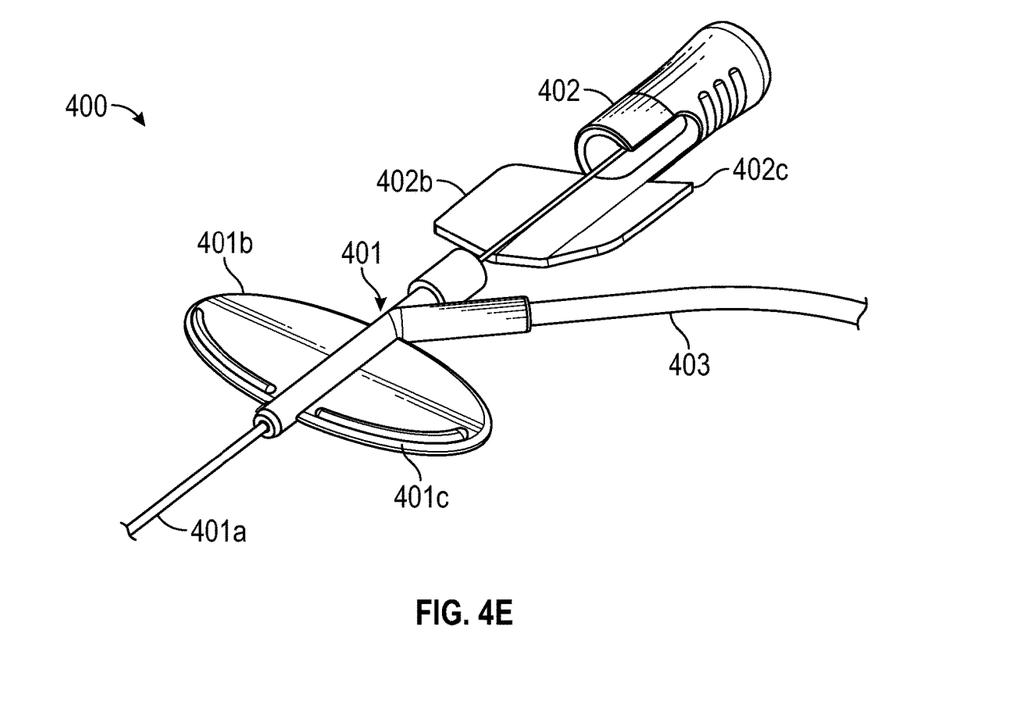

After catheter 401a has been inserted into the patient's vasculature, needle hub 400 can be withdrawn from catheter adapter 401 as shown in FIG. 4E. With needle hub 400 withdrawn, wings 401b and 401c can return to their flat orientation (e.g., an orientation within a common plane) and secured to the patient (e.g., via tape).

Figure 5A:
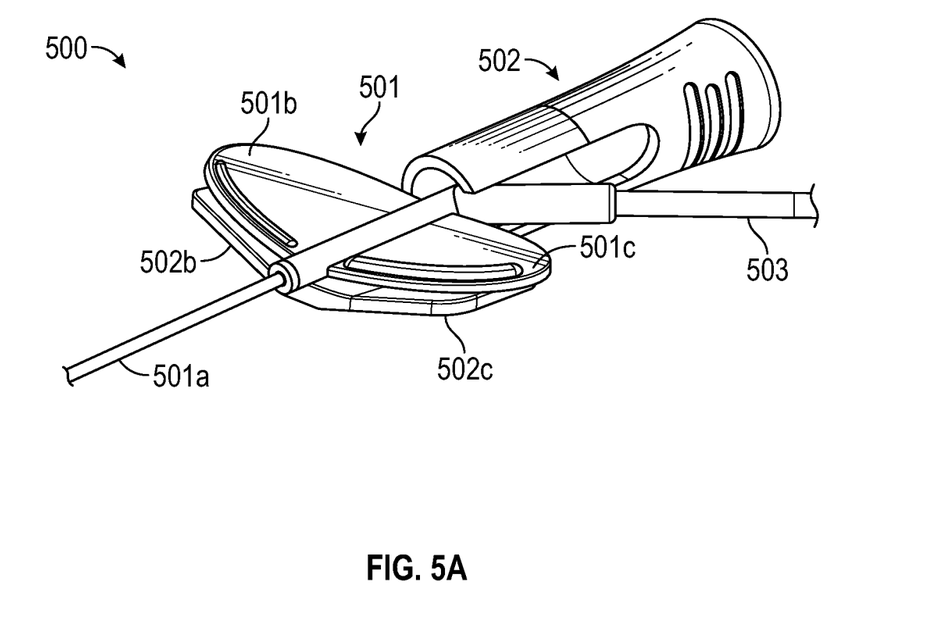
FIGS. 5A and 5B illustrate various views of another access device configured in accordance with one or more embodiments of the present invention.
Figure 5B:
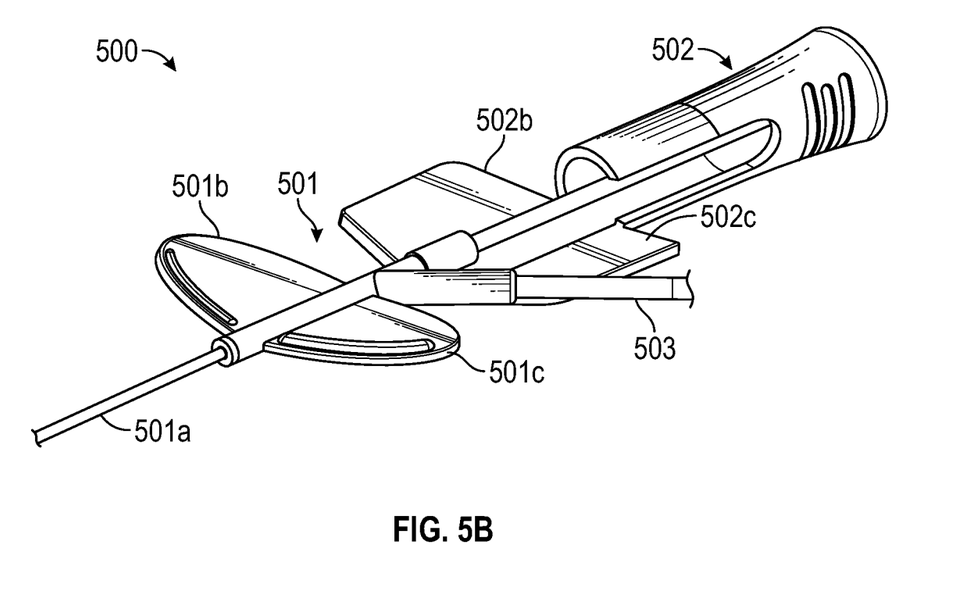

FIGS. 5A and 5B illustrate an access device 500 that is substantially similar to access device 400. Access device 500 includes a catheter adapter 501 having a catheter 501a and wings 501b and 501c, a needle hub 502 having paddle grips 502b and 502c, and an extension tube 503. Paddle grips 502b and 502c can function in a similar manner as paddle grips 402b and 402c. However, as best shown in FIG. 5A, paddle grips 502b and 502c are shaped in a similar manner as wings 501b and 501c. In contrast, as best shown in FIGS. 4A and 4B, paddle grips 402b and 402c are shorter than wings 401b and 401c, only extending outwardly about half the distance that wings 401b and 401c extend.

It is noted that although the configuration of needle hub 400 and needle hub 500 are different than the configuration of needle hub 200, needle hub 200 may also be configured to include a second paddle grip similar to and opposite paddle grip 202b. In such cases, needle hub 200 could function as described above to position wings 201b and 201c in an angled orientation.

Figure 6A:
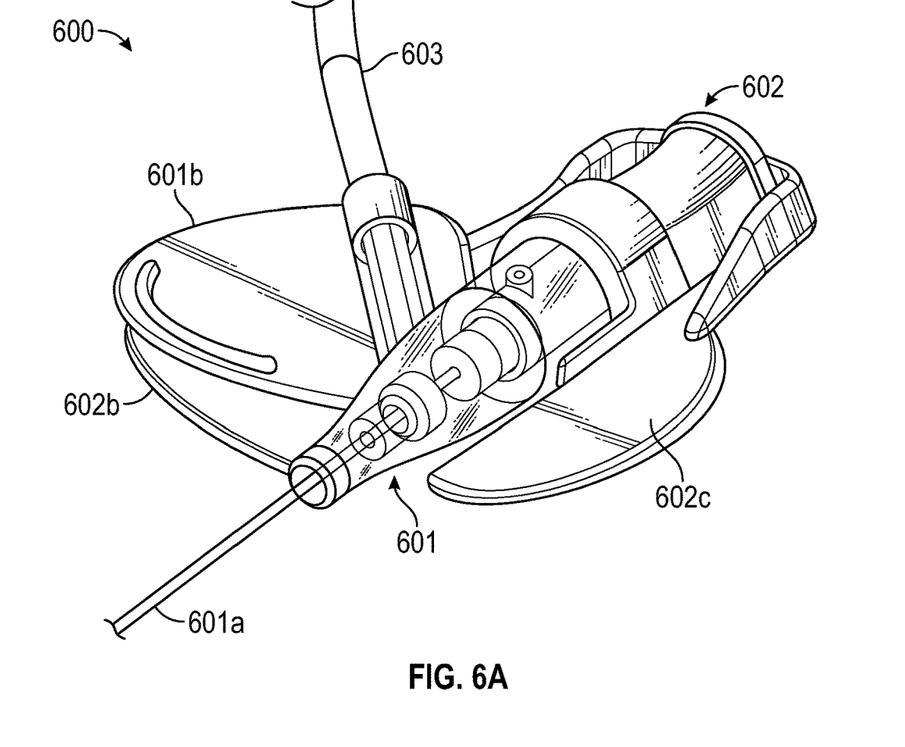
FIGS. 6A and 6B illustrate various views of another access device configured in accordance with one or more embodiments of the present invention.
Figure 6B:
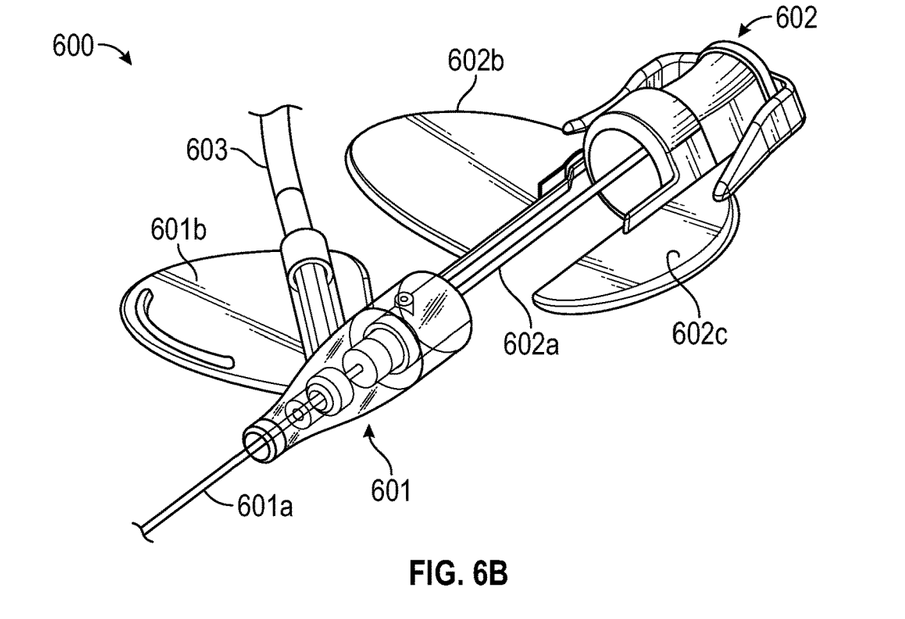

In some embodiments, a needle hub may include a paddle grip even though the catheter adapter may not have a corresponding wing. FIGS. 6A and 6B illustrate an example of an access device 600 that is configured in this manner. In FIG. 6A, needle hub 602 is shown as being coupled to catheter adapter 601 while in FIG. 6B needle hub 602 is shown as being decoupled from catheter adapter 601.

Catheter adapter 601 includes a catheter 601a and a single wing 601b that extends outwardly from a right side of the catheter adapter. An interface for coupling an extension tube 603 to catheter adapter 601 is formed within wing 601b. Although catheter adapter 601 includes only a single wing 601b, needle hub 602, from which needle 602a extends, includes paddle grips 602b and 602c that are configured to be positioned on opposite sides of catheter adapter 601 when needle hub 602 is coupled to catheter adapter 601. Paddle grip 602b generally corresponds to the shape of wing 601b and is angled such that it lifts wing 601b into an angled orientation. Paddle grip 602c may be configured in a flat orientation or in an angled orientation (e.g., as with paddle grip 402c and 502c). By including paddle grip 602c, the clinician has the option of positioning catheter adapter 601 in the orientation shown in FIG. 6B or of rotating catheter adapter 601 with respect to needle hub 602 so that wing 601b is adjacent wing 602c. Rotating catheter adapter 601 in this manner would allow the clinician to grip access device 600 on the left side (as opposed to on the right side when catheter adapter 601 is positioned as shown in FIG. 6A) during insertion of catheter 601a.

Figure 7A:
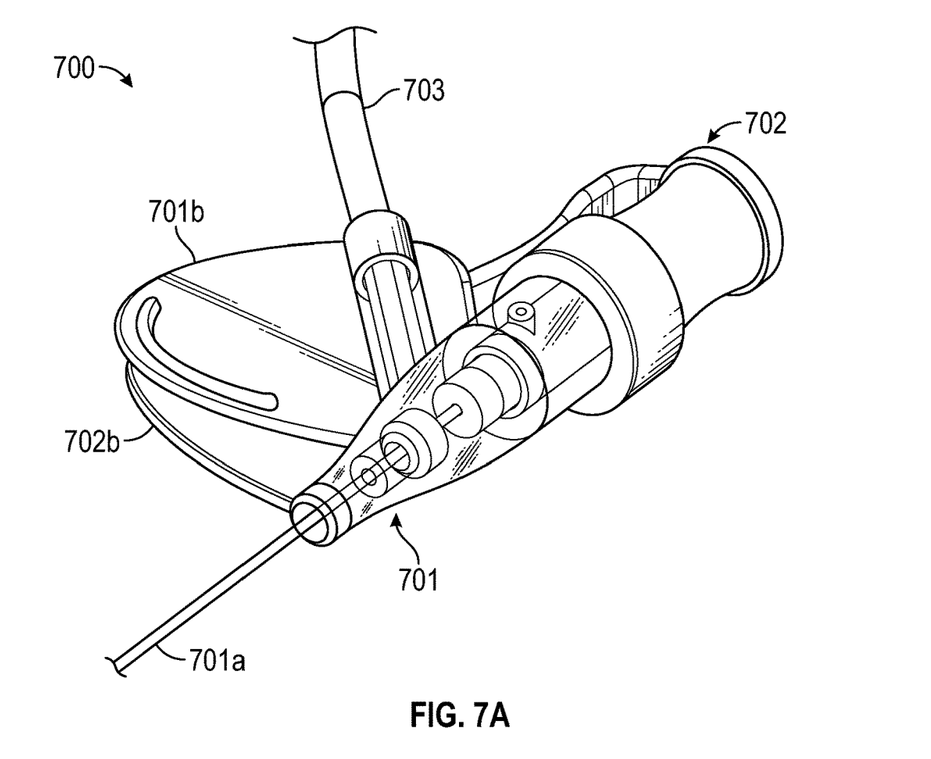
FIGS. 7A and 7B illustrate various views of another access device configured in accordance with one or more embodiments of the present invention.
Figure 7B:
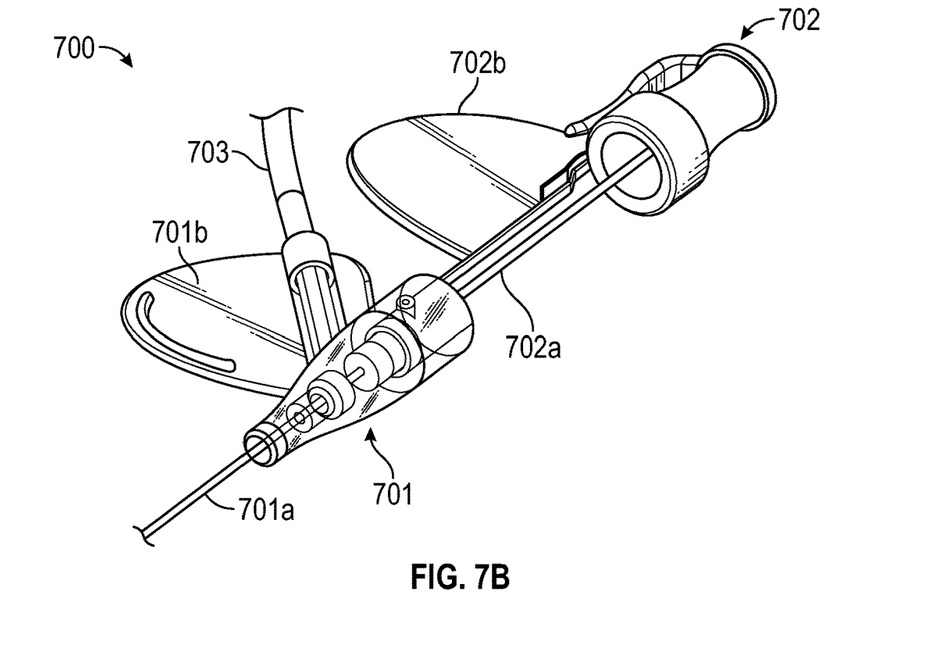

FIGS. 7A and 7B illustrate an access device 700 that includes a single paddle grip and a single wing on the same side as the extension tubing. Access device 700 includes a catheter adapter 701 from which a catheter 701a extends distally. Catheter adapter 701 also includes a wing 701b and extension tubing 703 that extends from catheter adapter 701 on the same side as wing 701b. Access device 700 also includes a needle hub 702 from which a needle 702a extends distally and a paddle grip 702b that is oriented at an angle so that wing 701b can also be oriented at an angle when paddle grip 702b is positioned adjacent (e.g., under) wing 701b. Access device 700 is therefore similar to access device 600 except that needle hub 702 does not include a second wing similar to wing 602c. Although not depicted, it is possible that access device 700 could be configured such that extension tubing 703 couples to catheter adapter 701 on a side opposite wing 701b.

In summary, the present invention is generally directed to access devices that include needle hubs having one or more angled paddle grips for positioning one or more wings of a catheter adapter's stabilization platform in an angled orientation. By positioning a wing in an angled orientation, the insertion of the catheter at a low angle is facilitated.

Various embodiments of the present invention further comprise a safety mechanism configured to secure the sharpened, distal tip of the introducer needle following removal and separation of the needle hub from the catheter adapter. A safety mechanism may include any compatible device known in the art. In some instances, the safety mechanism is configured to interact with a needle feature, such as a ferrule, notch, crimp or bump on the cannula. The crimp or bump formed in the cannula causes a slight out of round configuration that can be used to activate a safety mechanism. In some instance, the safety mechanism comprises an arm or lever that is actuated to capture the needle tip within the mechanism and prevent the tip from emerging prior to safe disposal.

The safety mechanism is attached to the body of the needle and is capable of sliding along the length thereof. In some instances, an initial or assembled position of the safety mechanism is located in proximity to the base or proximal end of the catheter adapter prior to catheterization. For some configurations, the assembled position of the safety mechanism is between the proximal end of the needle hub and the proximal end of the catheter adapter or stabilization platform, wherein the safety mechanism does not overlap the catheter adapter or stabilization platform. In some instances, a portion of the safety mechanism is positioned within the catheter adapter, with the balance of the safety mechanism being positioned external to the catheter adapter, such as within the needle hub. In some embodiments, a portion of the catheter adapter or stabilization platform is extended proximally to provide a housing in which at least a portion of the safety mechanism is housed. In some instances, the entire safety mechanism is housed within the housing of the catheter adapter or stabilization platform prior to catheterization.

In some embodiments, the assembled position of the safety mechanism positions the proximal end of the catheter adapter between the distal end of the safety mechanism and a distal end of a paddle grip of the needle hub. In some instances, the assembled position of the safety mechanism positions the proximal end of the catheter adapter between the distal end of the safety mechanism and a proximal end of a paddle grip of the needle hub. In some instances, a portion of the safety mechanism overlaps a portion of a paddle grip of the needle hub. In some embodiments, at least some portion of at least one of the catheter adapter and the paddle grip overlaps at least some portion of the safety mechanism. In some embodiments, no portion of the catheter adapter or paddle grip overlaps any portion of the safety mechanism.

In some embodiments, a defeatable mechanical connection is provided between the safety mechanism and at least one other component of the access device. In some embodiments, a distal end of the safety mechanism is selectively coupled to a proximal end of the catheter adapter. In one embodiment, the safety mechanism interlocks internally to the proximal end of the catheter adapter. In one embodiment, the safety mechanism interlocks externally to the proximal end of the catheter adapter. In some embodiments, a distal end of the safety mechanism is selectively coupled to a proximal end of the stabilization platform. In some embodiments, a surface of the safety mechanism is selectively coupled to at least one surface of at least one of the catheter adapter, a blood control valve, an extension tube, and the stabilization platform. In some instances, the mechanical connection is defeated upon securement of the needle tip within the safety mechanism.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An IV access device comprising:
   a catheter adapter from which a catheter extends distally, the catheter adapter including a wing; and
   a needle hub from which a needle extends distally, the needle hub being configured to be coupled to the catheter adapter such that the needle extends through the catheter;
   wherein the needle hub further includes a paddle grip oriented at an angle and configured to lift the wing to a corresponding angle.

2. The IV access device of claim 1, wherein the wing is formed of a flexible material that allows the wing to pivot from a flat orientation into an angled orientation when the paddle grip is adjacent the wing.

3. The IV access device of claim 1, wherein the wing is coupled to the catheter adapter via a hinged connection, the hinged connection allowing the wing to pivot from a flat orientation to an angled orientation when the paddle grip is adjacent the wing.

4. The IV access device of claim 1, wherein, when the needle hub is not coupled to the catheter adapter, the wing is positioned in a flat orientation.

5. The IV access device of claim 1, wherein the wing is a first wing, the catheter adapter further comprising a second wing that is positioned opposite the first wing.

6. The IV access device of claim 5, wherein the paddle grip is a first paddle grip, the needle hub further comprising a second paddle grip that is positioned opposite the first paddle grip.

7. The IV access device of claim 6, wherein the second paddle grip is oriented at an angle.

8. The IV access device of claim 6, further comprising:
   an extension tube coupled to the catheter adapter.

9. The IV access device of claim 8, wherein the extension tube is coupled to the second wing.

10. The IV access device of claim 1, wherein the paddle grip is a first paddle grip, the needle hub further comprising a second paddle grip that is positioned opposite the first paddle grip.

11. The IV access device of claim 1 wherein the needle hub further comprises a flash chamber at a proximal end of the needle hub, a proximal end of the needle being in fluid communication with the flash chamber.

12. The IV access device of claim 1, wherein the paddle grip is oriented at an angle that causes the wing to be substantially parallel with the paddle grip when the paddle grip is adjacent the wing.

13. The IV access device of claim 1, wherein the wing is a first wing and the catheter adapter comprises a second wing opposite the first wing, the second wing being positioned in a flat orientation when the paddle grip positions the first wing in an angled orientation.

14. The IV access device of claim 1, wherein the wing extends outwardly beyond the paddle grip.

15. The IV access device of claim 1, wherein the paddle grip extends outwardly beyond the wing.

16. An IV access device comprising:
   a catheter adapter from which a catheter extends distally, the catheter adapter including a wing; and
   a needle hub from which a needle extends distally, the needle hub being configured to be coupled to the catheter adapter such that the needle extends through the catheter;
   wherein the needle hub further includes a paddle grip that is configured to be positioned adjacent the wing when the needle hub is coupled to the catheter adapter, wherein, when the paddle grip is forced into contact with the wing, the paddle grip causes the wing to be elevated into an angled orientation.

17. The IV access device of claim 16, wherein the paddle grip is forced into contact with the wing when the paddle grip and wing are squeezed between a thumb and finger of a clinician during insertion of the catheter.

18. The IV access device of claim 16, wherein the wing is a first wing, the catheter adapter comprising a second wing positioned opposite the first wing, the second wing incorporating an extension tube.

19. An IV access device comprising:
   a catheter adapter from which a catheter extends distally, the catheter adapter including a first wing that extends from a first side of the catheter adapter and a second wing that extends from a second side of the catheter adapter opposite the first side;
   an extension tube that couples to the catheter adapter on the second side; and
   a needle hub from which a needle extends distally, the needle hub being configured to be coupled to the catheter adapter such that the needle extends through the catheter, the needle hub including a paddle grip that is configured to be positioned adjacent the first wing when the needle hub is coupled to the catheter adapter, wherein the paddle grip oriented at an angle and configured to lift the first wing to a corresponding angle.

20. The IV access device of claim 19, wherein the first and second wing are configured to extend outwardly within a common plan, the paddle grip causing the first wing to be positioned at an angle with respect to the common plane.

* * * * *